US008586496B2

(12) United States Patent
Duncan et al.

(10) Patent No.: US 8,586,496 B2
(45) Date of Patent: Nov. 19, 2013

(54) PREPARATION OF MOLECULAR SIEVE CATALYSTS AND THEIR USE IN THE PRODUCTION OF ALKYLAROMATIC HYDROCARBONS

(75) Inventors: Carolyn B. Duncan, Franklin, GA (US); Jon E. R. Stanat, Westhampton Beach, NY (US); Daria N. Lissy, Glen Mills, PA (US); Jane C. Cheng, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 354 days.

(21) Appl. No.: 12/997,339

(22) PCT Filed: Jun. 19, 2009

(86) PCT No.: PCT/US2009/048000
§ 371 (c)(1),
(2), (4) Date: Jan. 31, 2011

(87) PCT Pub. No.: WO2010/011451
PCT Pub. Date: Jan. 28, 2010

(65) Prior Publication Data
US 2011/0118521 A1    May 19, 2011

Related U.S. Application Data

(60) Provisional application No. 61/082,710, filed on Jul. 22, 2008.

(51) Int. Cl.
*B01J 29/06* (2006.01)
*C07C 2/66* (2006.01)

(52) U.S. Cl.
USPC ........ 502/60; 502/8; 502/62; 502/63; 502/64; 502/87; 502/507; 502/527.14; 585/435; 585/446; 585/467; 585/455

(58) Field of Classification Search
USPC .......... 502/8, 60, 62, 63, 64, 87, 507, 527.14; 585/435, 446, 467, 455
See application file for complete search history.

(56) References Cited

U.S. PATENT DOCUMENTS

| | | |
|---|---|---|
| 3,293,192 A | 12/1966 | Maher et al. |
| 3,308,069 A | 3/1967 | Wadlinger et al. |
| 3,442,795 A | 5/1969 | Kerr et al. |
| 3,449,070 A | 6/1969 | McDaniel et al. |
| 3,702,886 A | 11/1972 | Argauer et al. |
| 3,709,979 A | 1/1973 | Chu |
| 3,766,093 A | 10/1973 | Chu |
| 3,832,449 A | 8/1974 | Rosinski et al. |
| RE28,341 E | 2/1975 | Wadlinger et al. |
| 3,894,104 A | 7/1975 | Chang et al. |
| 3,923,636 A | 12/1975 | Mead et al. |
| 3,972,983 A | 8/1976 | Ciric |
| 4,016,218 A | 4/1977 | Haag et al. |
| 4,016,245 A | 4/1977 | Plank et al. |
| 4,076,842 A | 2/1978 | Plank et al. |
| RE29,948 E | 3/1979 | Dwyer et al. |
| 4,234,231 A | 11/1980 | Yan |
| 4,401,556 A | 8/1983 | Bezman et al. |
| 4,439,409 A | 3/1984 | Puppe et al. |
| 4,556,477 A | 12/1985 | Dwyer |
| 4,826,667 A | 5/1989 | Zones et al. |
| 4,954,325 A | 9/1990 | Rubin et al. |
| 5,026,933 A | 6/1991 | Blain et al. |
| 5,191,135 A | 3/1993 | Dwyer et al. |
| 5,236,575 A | 8/1993 | Bennett et al. |
| 5,256,277 A | 10/1993 | Del Rossi et al. |
| 5,362,697 A | 11/1994 | Fung et al. |
| 5,779,882 A * | 7/1998 | Chester et al. ........... 208/120.01 |
| 5,833,739 A | 11/1998 | Klatte et al. |
| 6,077,498 A | 6/2000 | Diaz Cabanas et al. |
| 6,180,549 B1 * | 1/2001 | Mazany et al. ................. 502/64 |
| 6,294,498 B1 | 9/2001 | Darcissac et al. |
| 6,583,096 B1 | 6/2003 | Kott et al. |
| 6,756,030 B1 | 6/2004 | Rohde et al. |
| 2003/0171204 A1 | 9/2003 | Winder et al. |
| 2005/0165264 A1 | 7/2005 | Duncan et al. |
| 2008/0039668 A1 | 2/2008 | Dandekar et al. |

FOREIGN PATENT DOCUMENTS

| | | |
|---|---|---|
| EP | 0 293 032 | 11/1988 |
| JP | 61295226 | 12/1986 |
| WO | 91/15443 | 10/1991 |

(Continued)

OTHER PUBLICATIONS

Aguilar et al., "Alkylation of biphenyl with propylene using MCM-22 and ITQ-2 zeolites", Catalysis Today, Elsevier, vol. 133-135, pp. 667-672 (2008).

Corma et al., "Characterization and Catalytic Activity of MCM-22 and MCM-56 Compared with ITQ-2", Journal of Catalysis, Academic Press, vol. 191, No. 1, pp. 218-224 (2000).

Dumitriu et al., "Liquid-phase alkylation of phenol with t-butanol over various catalysts derived from MWW-type precursors", Comptes Rendus-Chimie, Elsevier SAS, vol. 8, No. 34, pp. 441-456 (2005).

(Continued)

*Primary Examiner* — Elizabeth Wood
(74) *Attorney, Agent, or Firm* — Darryl M. Tyus

(57) ABSTRACT

A method is described for preparing a molecular sieve-containing catalyst for use in a catalytic process conducted in a stirred tank reactor. The method comprises providing a mixture comprising a molecular sieve crystal and forming the mixture into catalyst particles having an average cross-sectional dimension of between about 0.01 mm and about 3.0 mm. The mixture may include a binder and the catalyst particles are then calcined to remove water therefrom and, after calcination and prior to loading the catalyst particles into a reactor for conducting the catalytic process, the catalyst particles are coated with a paraffin inert to the conditions employed in the catalytic process.

20 Claims, No Drawings

(56) References Cited

FOREIGN PATENT DOCUMENTS

| WO | 97/17290 | 5/1997 |
|---|---|---|
| WO | 00/15553 | 3/2000 |
| WO | 01/09067 | 2/2001 |
| WO | WO 2008/088659 | 7/2008 |

OTHER PUBLICATIONS

He et al., "Synthesis, characterization and catalytic activity of the pillared molecular sieve MCM-36", Microporous and Mesoporous Materials, Elsevier Science B.V., vol. 25, No. 1-3, pp. 207-224 (1998).

Inagaki et al., "Shape selectivity of MWW-type aluminosilicate zeolites in the alkylation of toluene with methanol", Applied Catalysis A, General, Elsevier B.V., vol. 318, pp. 22-27 (2007).

Zhang et al., "Alkylation of benzene with propylene over MCM-36: A comparative study with MCM-22 zeolite synthesized from the same precursors", Reaction Kinetics and Catalysis Letters, Akademiai Kiado, Budapest and Springer, Dordrecht, NL, vol. 90, No. 1, pp. 45-52 (2007).

* cited by examiner ically used as extrudates, typically in combination with a binder. As a result, molecular sieve catalysts tend to have limited surface area and hence activity, so that the alkylation reaction (normally conducted in a fixed bed

PREPARATION OF MOLECULAR SIEVE CATALYSTS AND THEIR USE IN THE PRODUCTION OF ALKYLAROMATIC HYDROCARBONS

PRIORITY CLAIM

This application is a National Stage Application of International Application No. PCT/US2009/048000 filed Jun. 19, 2009, which claims the benefit of prior U.S. Provisional Application Ser. No. 61/082,710 filed Jul. 22, 2008, both of which are hereby incorporated by reference in its their entirety.

FIELD

This invention relates to the preparation of molecular sieve catalysts and their use in the production of alkylaromatic hydrocarbons, especially long chain alkylaromatic hydrocarbons (in which the alkyl moiety contains at least 9 carbon atoms) for use in the production of sulfonate surfactants.

BACKGROUND

Today, there are two commercial processes in widespread use for the production of long chain alkylaromatic hydrocarbons. Both of these processes involve alkylating an aromatic compound, generally benzene, with a linear olefin in the presence of a homogeneous acid catalyst in a stirred batch reactor. In one process, the catalyst is $AlCl_3$ which is washed out of the reactor with waste water at the end of the reaction. In the other process the catalyst is HF which is distilled off and recovered for re-use at the end of the reaction. However, both of these processes suffer from a number of serious disadvantages. Firstly, both of the catalysts are very corrosive and have numerous safety and environmental issues associated with their use. Secondly, the surfactant industry has an increasing demand for alkylaromatic hydrocarbons in which the aromatic species is predominantly located at the 2- and 3-positions in the alkyl side chain, since 2- and 3-phenyl substituted alkylbenzene sulfonates exhibit superior performance as surfactants. However, alkylaromatic hydrocarbons made with $AlCl_3$ as the catalyst typically contain about 52% of the 2- and 3-phenyl isomers, whereas materials produced using HF as the catalyst generally only contain about 17% of the 2- and 3-phenyl isomers.

Molecular sieves, such as aluminosilicate zeolites, are also known to be effective acid catalysts for the production of alkylaromatic hydrocarbons, particularly short chain alkylaromatic hydrocarbons, such as ethylbenzene and cumene. In addition, molecular sieve catalysts are well known to offer significant advantages over $AlCl_3$ and HF, in that they are generally non-toxic and non-corrosive. Moreover, when used to alkylate aromatic compounds with linear and lightly branched long chain olefins, certain molecular sieves have been found to be effective in producing alkylaromatic hydrocarbons with very high levels, up to 95%, of the 2- and 3-phenyl isomers. See, for example, U.S. Pat. No. 5,026,933 and U.S. Patent Application Publication No. 2005/0165264.

However, molecular sieve catalysts suffer from a number of disadvantages which has to date limited their use as alkylation catalysts for the production of long chain alkylaromatic hydrocarbons. Firstly, to impart structural stability, molecular sieve catalysts are normally used as extrudates, typically in combination with a binder. As a result, molecular sieve catalysts tend to have limited surface area and hence activity, so that the alkylation reaction (normally conducted in a fixed bed tubular reactor) typically takes on the order of 24 hours to achieve at least 90% conversion of the olefin feed. Moreover, molecular sieves are generally hydrophilic and so must be dehydrated by calcination before use and, after dehydration, must be protected from the air to prevent absorption of water and resulting reduced activity.

Secondly, current molecular sieve catalysts are unsuitable for use in the stirred batch reactors used for the commercial production of long chain alkylaromatic hydrocarbons using homogeneous catalysts. In particular, the surface area of extrudates of molecular sieve catalysts is too small to produce any appreciable rate of reaction in a stirred reactor process. Further, the extrudates would tend to separate from the liquid phase reaction mixture and fall to the bottom of the reactor. Crushing the extrudates to reduce their particles size could be used to increase their surface area and activity. However, the resultant powder could not be calcined in a stirred batch reactor since, removing the water would generate a build-up of static electricity causing the catalyst to adhere to the walls of the reactor rather that being dispersed in the reaction mixture.

According to the present invention, there is provided a method of producing and using molecular sieve-containing catalyst particles suitable for use in the production of alkylaromatic hydrocarbons, particularly long chain alkylaromatic hydrocarbons, in, for example, stirred tank reactors. In this method, a mixture comprising molecular sieve crystals are formed into catalyst particles having an average cross-sectional dimension between about 0.01 mm and about 3.0 mm. The catalyst particles are coated with a liquid paraffin inert to the conditions employed in the alkylation reaction. The catalyst particles may also be combined with a binder before being formed and then calcined to remove water. The small size of the catalyst particles ensures sufficient activity for use, for example, in a stirred batch reactor, while the paraffinic coating helps to protect the particles against water adsorption prior to use as well as assisting in dispersion of the particles in the alkylation reaction medium.

It is to be appreciated that there are numerous references in the patent and academic literature to stirred reactors being used in bench-scale testing of zeolite catalysts in the production of long chain alkylaromatic hydrocarbons, see, for example, Example 3 of U.S. Pat. No. 6,583,096. However, in view of the problems discussed above, zeolite catalysts particles having an average cross-sectional dimension between about 0.01 mm and about 3.0 min have to date been considered unsuitable for use in commercial-scale, in, for example, stirred tank reactors, for producing long chain alkylaromatic hydrocarbons.

SUMMARY

In one aspect, the invention resides in a method of preparing a molecular sieve-containing catalyst for use in a catalytic process, the method comprising:

(a) providing a mixture comprising molecular sieve crystals;

(b) forming the mixture into catalyst particles having an average cross-sectional dimension of between about 0.01 mm and about 3.0 mm; and (c) coating the catalyst particles from (b) with a paraffin inert to the conditions employed in said catalytic process.

Conveniently, the catalyst particles have an average cross-sectional dimension of between about 0.01 mm and about 3.0 mm, preferably between about 0.01 mm and about 2.0 mm, and more preferably between about 0.01 mm and about 1.0 mm.

In another embodiment, the mixture further comprises a binder. The method further comprises the step of calcining the catalyst particles formed in (b) to remove water therefrom, prior to coating the catalyst particles.

In one embodiment, the mixture is formed directly into said catalyst particles. In another embodiment, the mixture is formed into an extrudate and the extrudate is crushed to produce said catalyst particles.

Conveniently, the catalyst particles are calcined at a temperature between about 150° and about 650° C., preferably between about 150° C. and about 500° C.

Conveniently, the paraffin is selected from decane, dodecane and mixtures thereof.

In a further aspect, the invention resides in a process for producing an alkylaromatic hydrocarbon, the process comprising:

(a) providing a mixture comprising molecular sieve crystals;

(b) forming the mixture into catalyst particles having an average cross-sectional dimension of between about 0.01 mm and about 3.0 mm, preferably between about 0.01 mm and about 2.0 mm, and more preferably between about 0.01 mm and about 1.0 mm;

(c) coating the catalyst particles with a paraffin inert to the conditions employed in the process; and (d) contacting an aromatic hydrocarbon with at least one olefin in the presence of said catalyst particles in a reactor under alkylation conditions to produce an effluent comprising said alkylaromatic hydrocarbon.

In one embodiment, the mixture further comprises a binder. The method further comprises the step of calcining the catalyst particles from (b) to remove water therefrom, and then loading the coated, catalyst particles from (c) into a reactor, preferably a stirred batch reactor.

In one embodiment, the above process further comprises separating said catalyst particles from said effluent and returning the separated particles to said reactor.

Conveniently, said aromatic hydrocarbon comprises benzene and said at least one olefin having at least 9 carbon atoms, preferably at least 10 carbon atoms. In one embodiment, said at least one olefin comprises a mixture of olefins each having at least 9 carbon atoms, preferably at least 10 carbon atoms and is produced by oligomerizing at least one of propene, butene and mixtures thereof.

Conveniently, said molecular sieve has an X-ray diffraction pattern including d-spacing maxima at 12.4±0.25, 6.9±0.15, 3.57±0.07 and 3.42±0.07 Angstroms and typically is selected from MCM-22, PSH-3, SSZ-25, ERB-1, ITQ-1, ITQ-2, MCM-36, MCM-49, MCM-56, UZM-8, and mixtures thereof.

Conveniently, the alkylation conditions include a temperature of from about 80° C. to about 250° C., a pressure of about 100 to about 3500 kPa and an aromatic compound to olefin mole ratio of about 1:1 to about 40:1, preferably about 1:1 to about 20:1.

Conveniently, the reactor has a capacity greater than 2 liters, such as greater than 10 liters, for example greater than 100 liters.

DETAILED DESCRIPTION

Described herein is a method of preparing a molecular sieve-containing catalyst for use in a catalytic process, the method comprising (a) providing a mixture comprising molecular sieve crystals; (b) forming the mixture of molecular sieve crystals into catalyst particles having an average cross-sectional dimension of between about 0.01 mm and about 3.0 mm, and (c) coating the catalyst particles with a paraffin inert to the conditions employed in said catalytic process. In some embodiments, the catalyst particles are calcined to remove water and to enable the resultant catalyst to be used in a commercial-scale reactor, such as a stirred tank reactor, particularly, but not exclusively, for producing long chain alkylaromatic hydrocarbons (namely those in which the alkyl moiety contains at least 9 carbon atoms). Such reactors would typically have a capacity greater than 2 liters, preferably greater than 10 liters, more preferably greater than 100 liters.

As used herein, the term "paraffin" includes linear and branched saturated alkane hydrocarbons with the general formula $C_nH_{2n+2}$, preferably paraffins having 7 to 30 carbon atoms, more preferably paraffins such as decane and dodecane.

Any molecular sieve can be used in the present method and in practice the particular molecular sieve employed will be selected according to the projected use of the final catalyst. For example, where the catalyst is to be used in the production of long chain alkylaromatic hydrocarbons, the molecular sieve is generally selected from (a) a medium pore molecular sieve having a Constraint Index of 2-12 (as defined in U.S. Pat. No. 4,016,218), (b) a large pore molecular sieves having a Constraint Index less than 2, and/or (c) a molecular sieve of the MCM-22 family.

Suitable medium pore molecular sieves include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

Suitable large pore molecular sieves include zeolite beta, faujasite, zeolite Y, Ultrastable Y (USY), Dealuminized Y (DealY), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Faujasite is a naturally occurring material, but is available in synthetic forms, such as X and Y zeolites. Zeolite beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof.

As synthesized, most molecular sieves comprise single or agglomerated crystals having an average diameter between about 0.05 micron and 50 micron, preferably between about 0.05 and 10 micron, more preferably between about 0.05 and about 1 micron, whereas it is found that improved results are obtained in non-fixed bed reactors, such as stirred tank reactors, when the molecular sieve crystals are formed into catalyst particles having an average cross-sectional dimension of between about 0.01 mm and about 3.0 mm, preferably between about 0.01 mm and about 2.0 mm, and more preferably between about 0.01 mm and about 1.0 mm. Moreover, most molecular sieve crystals are highly susceptible to attrition if used directly in non-fixed bed reactors, such as a stirred tank reactor. Thus, prior to forming into catalyst particles, the as-synthesized molecular sieve is composited with a binder which is resistant to the temperatures and other conditions employed in the alkylation reaction.

Suitable binder include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a binder material in conjunction with the molecular sieve, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and binder may vary widely, with the sieve content ranging from about 1 to about 90 percent by weight and more usually, particularly, when the composite is prepared in the form of beads, in the range of about 2 to about 80 weight percent of the composite.

After compositing with a binder, the molecular sieve is formed into catalyst particles, generally by initially extruding the molecular sieve/binder mixture into shaped extrudates. Most commercial extruders produce cylindrical extrudates with a diameter of between about 1.0 mm and about 4.5 mm, preferably between about 1.4 mm and about 4.5 mm, and a length of between about 1.4 mm and about 10 mm. Thus, after drying, the extrudates are typically crushed and sieved to yield the desired catalyst particles having an average cross-sectional dimension of between about 0.01 mm and about 3.0 mm, preferably between about 0.01 mm and about 2.0 mm, more preferably between about 0.01 mm and about 3.0 mm. Alternatively, the molecular sieve/binder mixture can be formed directly into catalyst particles of the desired size, such as by pelletization or spray drying.

After being formed to the correct size, the catalyst particles are calcined to remove at least part of the water present in the catalyst particles either from the hydrothermal synthesis process used in producing the molecular sieve crystals or from the extrusion process used in producing the shaped particles or both. Typically, the calcination is conducted in dry air at a temperature between about 150° C. and 650° C., preferably between about 150° C. and about 500° C. for a time between about 30 minutes and about 12 hours to reduce the water level in the catalyst particles.

After calcination, the catalyst particles are allowed to cool to room temperature and are then coated with a paraffin. The paraffin is not particularly limited and is substantially in the liquid phase under the coating conditions and is substantially inert to the conditions to be employed in the subsequent catalytic process. Preferably, suitable paraffins include decane and dodecane. Coating of the catalyst particles is conveniently achieved by mixing the catalyst particles with the paraffin for a time between about 10 seconds and 180 minutes, preferably between about 10 seconds and about 60 minutes.

The coated catalyst particles can then be loaded into a reactor, such as a stirred tank reactor, for effecting the desired catalytic reaction. The paraffinic coating helps to protect the particles against water adsorption prior to use, but generally the reactor is kept under a nitrogen blanket, or suitable protection against air and moisture contamination of the catalyst particles, before the feedstocks are loaded into the reactor.

Where the desired reaction is alkylation to produce a long chain alkylaromatic hydrocarbon, benzene or another aromatic precursor is loaded into the reactor and then the desired olefin can be added and the reactor contents stirred under the alkylation conditions required for the olefin to react with the aromatic precursor to produce an effluent comprising the target alkylaromatic compound. Suitable alkylation conditions maintain at least the aromatic precursor at least partially in the liquid phase and include a temperature of from about 80° C. to about 250° C., a pressure of about 100 kPa to about 3500 kPa, and an aromatic compound to olefinic hydrocarbon mixture mole ratio of from about 1:1 to about 20:1, or about 1:1 to about 10:1.

In an alternative embodiment, the reactor is operated in a slurry boiling reactor configuration, in which benzene or other aromatic precursor is continuously vaporized to remove the heat of reaction and facilitate temperature control. After cooling and condensation, the aromatic compound can be returned to the reactor.

When the reaction is complete, the alkylaromatic product can be recovered by separating the catalyst particles from the effluent; such as, for example, filtering the reactor contents through a micron filter maintained under a nitrogen blanket to protect the catalyst from air and moisture. The catalyst particles, which is retained by the filter, can then be back-washed into the reactor with the aromatic precursor and the reaction repeated.

The invention will now be more particularly described with reference to the following Examples.

Examples 1 to 4

A series of experiments were conducted in which benzene was alkylated in a stirred tank reactor with a n-$C_{12}$ olefin (Example 1) and with different olefinic fractions obtained by distillation of oligomerization products of butene over ZSM-23 (Example 2: near-linear $C_{12}$ olefin, Example 3: near-linear $C_{16}$ olefin, and Example 4: a bottom fraction containing near-linear $C_{12}$, $C_{16}$ and $C_{20}^+$ olefins). The alkylation was conducted at 180° C., 150 psig (1135 kPa), 15:1 benzene/olefin molar ratio, and 20 wt % of an MCM-22 catalyst relative to the total olefins used. The MCM-22 catalyst, wetted with decane, was loaded into the reactor followed by benzene. The reactor was heated to the desired temperature, the olefin feed was then introduced, and the reactor pressure was adjusted by $N_2$.

The results are shown in Tables 1 to 4. Benzene and decane are excluded from the calculations. The results show that the solvent coated catalyst was effective to convert $C_{12}$-$C_{20}$ olefins to the corresponding alkylbenzene products. When comparing the 20 hrs data in Tables 1 and 2, the n-$C_{12}$ feed produced more alkylbenzene products than the near-linear $C_{12}$ feed due to increased branching of the near-linear $C_{12}$ feed. As the chain length of olefin feed increases from $C_{12}$ to $C_{16}$ to $C_{20}^+$ the alkylbenzene products found in the reactor (see the 20 hrs data in Tables 2 to 4) continue to decrease again due to increased branching of the olefin feed. These trends are expected since branched olefins are less active than linear olefins for alkylation with aromatics.

TABLE 1

Benzene alkylation with n-$C_{12}$ olefin (Example 1)

| Run Time (hrs) | % Lights | % $C_{12}$= | % $C_{16}$= | % $C_{20}$+= | % Alkylbenzene | % Heavies[b] |
|---|---|---|---|---|---|---|
| 0[a] | 0.66 | 37.59 | 0.21 | 0 | 60.05 | 1.49 |
| 5 | 1.27 | 7.73 | 0.11 | 0 | 88.76 | 2.13 |
| 10 | 1.41 | 3.93 | 0.14 | 0 | 92.26 | 2.28 |
| 20 | 1.26 | 2.53 | 0.13 | 0 | 93.81 | 2.26 |
| 24 | 1.19 | 2.40 | 0.14 | 0 | 93.79 | 2.48 |

[a]Zero run time indicates the first GC analysis run as soon as olefin was added to reactor
[b]Heavies include $C_{20}^+$ alkylbenzenes and traces of olefin dimer.

TABLE 2

Benzene alkylation with near-linear $C_{12}$ olefinic fraction (Example 2)

| Run Time (hrs) | % Lights | % $C_{12}$= | % $C_{16}$= | % $C_{20}$+= | % Alkylbenzene | % Heavies[b] |
|---|---|---|---|---|---|---|
| 0[a] | 0.99 | 51.88 | 0.89 | 0 | 39.20 | 7.04 |
| 5 | 1.16 | 7.27 | 1.28 | 0 | 82.63 | 7.66 |
| 10 | 1.52 | 6.11 | 1.51 | 0 | 82.66 | 8.20 |
| 20 | 1.44 | 5.98 | 1.60 | 0 | 83.82 | 7.16 |

[a]Zero run time indicates the first GC analysis run as soon as olefin was added to reactor
[b]Heavies include $C_{20}^+$ alkylbenzenes and traces of olefin dimer.

TABLE 3

Benzene alkylation with near-linear $C_{16}$ olefinic fraction (Example 3)

| Run Time (hrs) | % Lights | % $C_{12}$= | % $C_{16}$= | % $C_{20}$+= | % Alkylbenzene | % Heavies[b] |
|---|---|---|---|---|---|---|
| 0[a] | 0.50 | 2.15 | 56.93 | 4.30 | 26.68 | 7.44 |
| 5 | 1.65 | 1.63 | 9.89 | 3.05 | 75.98 | 7.80 |
| 10 | 2.35 | 1.92 | 5.82 | 3.68 | 78.14 | 8.10 |
| 20 | 2.29 | 2.05 | 5.14 | 3.34 | 79.04 | 8.14 |

[a]Zero run time indicates the first GC analysis run as soon as olefin was added to reactor
[b]Heavies include $C_{20}^+$ alkylbenzenes and traces of olefin dimer.

TABLE 4

Benzene alkylation with the bottom fraction (Example 4)

| Run Time (hrs) | % Lights | % $C_{12}$= | % $C_{16}$= | % $C_{20}$+= | % Alkylbenzene | % Heavies[b] |
|---|---|---|---|---|---|---|
| 0[a] | 1.00 | 35.70 | 26.17 | 7.75 | 21.11 | 8.25 |
| 5 | 1.46 | 26.31 | 21.55 | 7.48 | 32.96 | 10.25 |
| 10 | 1.93 | 11.75 | 10.85 | 5.40 | 55.81 | 14.26 |
| 20 | 2.35 | 5.31 | 5.36 | 4.05 | 64.51 | 18.42 |

[a]Zero run time indicates the first GC analysis run as soon as olefin was added to reactor
[b]Heavies include $C_{20}^+$ alkylbenzenes and traces of olefin dimer.

All documents described herein are incorporated by reference herein, including any priority documents and/or testing procedures to the extent they are not inconsistent with this text. While there have been described what are presently believed to be the preferred embodiments of the present disclosure, those skilled in the art will realize that other and further embodiments can be made without departing from the spirit of the disclosure, and is intended to include all such further modifications and changes as come within the true scope of the claims set forth herein.

The invention claimed is:

1. A process for preparing a paraffin-coated catalyst comprising molecular sieve-containing catalyst particles for use in a catalytic process comprising the steps of:
    (a) providing a mixture comprising molecular sieve crystals,
    (b) forming said mixture into molecular sieve-containing catalyst particles having an average cross-sectional dimension of between about 0.01 mm and about 3.0 mm,
    (c) coating said molecular sieve-containing catalyst particles with a paraffin to form said paraffin-coated catalyst, said paraffin is inert to the conditions employed in said catalytic process, wherein said coating of said molecular sieve-containing catalyst particles occurs outside of a vessel in which a reaction will occur, wherein said molecular sieve crystals are of the MCM-22 family having an X-ray diffraction pattern including d-spacing maxima at 12.4±0.25, 6.9±0.15, 3.57±0.07 and 3.42±0.07 Angstroms.

2. The process of claim 1, wherein said molecular sieve crystals of said MCM-22 family are selected from the group consisting of MCM-22, PSH-3, SSZ-25, ERB-1, ITQ-1, ITQ-2, MCM-36, MCM-49, MCM-56, UZM-8, and mixtures thereof 3. The process of claim 1, wherein said mixture further comprises a binder and said molecular sieve-containing catalyst particles have a cross-sectional dimension of between about 0.01 mm and about 1.0 mm.

4. The process of claim 3, further comprising the step of calcining said molecular sieve-containing catalyst particles produced in forming step (b) to remove water therefrom.

5. The process of claim 4, wherein said binder is selected from the group consisting of alumina, silica, titania and mixtures thereof.

6. The process of claim 1, wherein said mixture of step (b) is formed into an extrudate and the extrudate is crushed to produce said catalyst particles.

7. The process of claim 1, wherein said molecular sieve-containing catalyst particles are calcined at a temperature between about 150° C. and about 650° C. before the addition of a paraffin in coating step (c).

8. The process of claim 1, wherein said paraffin is either a linear or branched paraffin that contains between 7 and 30 carbon atoms.

9. A process for producing an alkylaromatic hydrocarbon comprising:
(a) providing a mixture comprising molecular sieve crystals;
(b) forming said mixture into molecular sieve-containing catalyst particles having an average cross-sectional dimension of between about 0.01 mm and about 3.0 mm;
(c) coating said molecular sieve-containing catalyst particles with a paraffin to form a paraffin-coated catalyst, said paraffin is inert to the conditions employed in said catalytic process, wherein said coating of said catalyst particles occurs outside of a reactor in which a reaction will occur, and wherein said molecular sieve crystals are of the MCM-22 family having an X-ray diffraction pattern including d-spacing maxima at 12.4±0.25, 6.9±0.15, 3.57±0.07 and 3.42±0.07 Angstroms;

(d) providing said paraffin-coated catalyst to said reactor;
(e) contacting an aromatic hydrocarbon with at least one olefin in the presence of said paraffin-coated catalyst in coating step (c) in said reactor under alkylation conditions to produce an effluent comprising said alkylaromatic hydrocarbon.

10. The process of claim 9, wherein said mixture further comprises a binder.

11. The process of claim 10 further comprising the steps prior to contacting step (e):
(f) calcining said molecular sieve-containing catalyst particles of forming step (b) to remove water therefrom;
(g) loading said calcined catalyst particles into said reactor.

12. The process of claim 11, wherein said reactor is a fixed bed reactor or a stirred tank reactor.

13. The process of claim 12, further comprising the steps of:
(h) separating said molecular sieve-containing catalyst particles from said effluent; and
(i) returning said catalyst particles to said reactor.

14. The process of claim 9, wherein said aromatic hydrocarbon comprises benzene.

15. The process of claim 9, wherein said olefin has at least 9 carbon atoms or said olefin comprises a mixture of olefins each having at least 9 carbon atoms.

16. The process of claim 15, wherein said mixture of olefins is produced by oligomerizing at least one of propene, butene and mixtures thereof 17. The process of claim 9, wherein said alkylation conditions in contacting step (d) include a temperature of about 80° C. to about 250° C., a pressure of about 100 to about 10000 kPa and an aromatic compound to olefin mole ratio of about 1:1 to about 50:1.

18. The process of claim 9, wherein said paraffin is either a linear or branched paraffin that contains between 7 and 30 carbon atoms.

19. The process of claim 18, wherein said paraffin is decane or dodecane.

20. The process of claim 8, wherein said paraffin is decane or dodecane.

* * * * *

UNITED STATES PATENT AND TRADEMARK OFFICE
CERTIFICATE OF CORRECTION

PATENT NO.        : 8,586,496 B2
APPLICATION NO.   : 12/997339
DATED             : November 19, 2013
INVENTOR(S)       : Duncan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 361 days.

Signed and Sealed this
Twenty-second Day of September, 2015

Michelle K. Lee
*Director of the United States Patent and Trademark Office*